US008865169B2

(12) United States Patent
Shoemaker et al.

(10) Patent No.: US 8,865,169 B2
(45) Date of Patent: Oct. 21, 2014

(54) METHODS AND SYSTEMS FOR MULTI-ANTIBODY THERAPIES

(75) Inventors: Charles B. Shoemaker, North Grafton, MA (US); Jorge A. Sepulveda Toepfer, Shrewsbury, MA (US); Jean Mukherjee, Worcester, MA (US)

(73) Assignee: Tufts University, Boston, MA (US)

( * ) Notice: Subject to any disclaimer, the term of this patent is extended or adjusted under 35 U.S.C. 154(b) by 1241 days.

(21) Appl. No.: 12/032,744

(22) Filed: Feb. 18, 2008

(65) Prior Publication Data
US 2010/0278830 A1   Nov. 4, 2010

Related U.S. Application Data

(60) Provisional application No. 60/890,626, filed on Feb. 20, 2007.

(51) Int. Cl.
*A61K 39/395* (2006.01)
*C07K 16/44* (2006.01)
*C07K 16/12* (2006.01)
*A61K 39/00* (2006.01)

(52) U.S. Cl.
CPC ....... *C07K 16/1282* (2013.01); *A61K 39/39591* (2013.01); *C07K 16/44* (2013.01); *C07K 2317/622* (2013.01); *C07K 2316/96* (2013.01); *A61K 2039/505* (2013.01); *C07K 2319/40* (2013.01)
USPC .................................................... 424/135.1

(58) Field of Classification Search
None
See application file for complete search history.

(56) References Cited

U.S. PATENT DOCUMENTS

| 5,194,596 | A | * | 3/1993 | Tischer et al. | 530/399 |
| 5,196,193 | A | * | 3/1993 | Carroll | 424/172.1 |
| 2006/0018911 | A1 | | 1/2006 | Ault-Riche et al. | |

OTHER PUBLICATIONS

Stancovski et al, Proceedings of the National Academy of Science USA 88: 8691-8695, 1991.*
Riemer et al, Mol. Immunol. 42: 1121-1124, 2005.*
Cogburn et al., Journal of Nutrition 119:1213.*
Yu et al, Investigative Ophthalmology & Visual Science 49(2): 522-527, Feb. 2008.*
Yu et al., Investigative Ophthalmology & Visual Science 49(2): 522-527, Feb. 2008.*
Jubala et al., Vet Pathol 42: 468-476, 2005.*
Witte et al., Cancer and Metastasis Reviews 17: 155-161, 1998.*
M. Clark. "Animal Models" 1998 [retrieved online May 23, 2008]. Retrieved from the Internet URL: http://www.path.cam.ac.uk/~mrc7/iggfunctions/models.html.
A. Nowakowski et al. "Potent neutralization of botulinum nourotoxin by recombinant oligoclonal antibody", PNAS, 99(17):11346-11350 (Aug. 20, 2000).
Cohn, M., and Langman, R.E., "The immune system: A look from a distance", Frontiers in Bioscience 1, d318-323 (Oct. 1, 1996).
Tonegawa, S., "The genetic principle for generation of antibody diversity", The Nobel Assembly at the Karolinska Institute [online], 1987 [retrieved on May 23, 2008]. Retrieved from the Internet <URL:http://nobelprize.org/nobel_prizes/medicine/laureates/1987/press.html>.

* cited by examiner

*Primary Examiner* — Phuong Huynh
(74) *Attorney, Agent, or Firm* — Lawson & Weitzen LLP; Sonia K. Guterman; Preeti T. Arun

(57) ABSTRACT

The present invention relates to methods and systems for administering antibody therapeutic agents. The methods include administering one or more (e.g., two or three) binding agents, wherein each of the binding agents has a binding region that is specific to a portion of a disease agent and one or more copies of a tag. The binding agents can be specific to one or more portions of the same or different disease agents. The tag is the same for each of the binding agents. The methods include administering an anti-tag antibody, wherein the anti-tag antibody has an anti-tag region that is specific to the tag, and can have an immunoglobulin (e.g., IgA, IgD, IgE, IgG, and IgM.). Disease agents include bacterial proteins, viral proteins, cancer cells, and proteins or toxins produced therefrom. In particular, the present invention includes methods and systems for binding agents that are specific to neurotoxins that cause botulism.

2 Claims, 6 Drawing Sheets

Anti-BoNT/A sheep scFv coding sequences

>scFv#2
CAGGCTGTGCTGACTCAGCCGTCCTCCGTGTCCGGGTCCCCGGGCCNNANGG
TCTCCATCACCTGCTCTGGAAGCAGGAGTAACGTTGGCACATATGGTGTAGG
TTGGTTCCAACAGCTCCCAGGATCGGGCCTCAGAACCATCATCTATTATAATG
ACAAACGACCCTCAGGGGTCCCCGACCGATTCTCTGCCTCCAAATCGGGCAA
CACAGCCACCCTGATCATCAGCTCGCTCCAGGCTGAGGATGAGGCCGATTAT
TTCTGTGGAAGTGCCGACGGTAGTAGTTATGGTATTTTCGGCAGTGGGACCA
GACTGACCGTCCTGGGTCAGCCCGCGGCCGCTGGTGGAGGCGGTTCAGGCGG
AGGTGGCTCTGGCGGTGGCGGATCGGCGCGCCAGGTGGGGCTGCAGGAGTCG
GGACCCAGCCTGGTGAAGCCCTCACAGACCCTCTCCCTCACCTGCACGGTCTC
TGGATTCTCATTGTCCAACAGTGTTGTAGGCTGGGTCCGCCAGGCTCCAGGAA
AGGTGCCGGAGTGGCTTGGTAGTATAGACAGTGGTGGTTACACAGTCGCTGA
CCCGGCCCTGAAATCCCGACTCAGCATCACAAGGGACACTTCCAAGAGCCAA
GTCTCCCTGTCACTGAACAGCGTGACAACTGAGGACACGGCCGTGTACTACT
GTACAAGGGCTTATAGTATTACTTATTATGCGTATCCCCCTATATCGACTAC
TGGGGCCCAGGACTCCTGGTCACCGTCTCCTCAACTAGTGGTGCGCCGGTGC
CGTATCCGGATCCGCTGGAACCGCGTGCCGCA (SEQ ID NO:1)

>scFv#3
CAGGCTGTGCTGACTCAGCCGTCCTCCGTGTCCAGGTCCCTGGGCCAGAGTGT
CTCCATCACCTGCTCTGGAAGCAGCAGCAACGTTGGATATGGTGATTATGTG
GGCTGGTTCCAACGGGTCCCAGGATCAGCCCCCAAACTCCTCATCTATGGTG
CAACCACTCGAGCCTCGGGGGTCCCCGACCGATTCTCCGGCTCCAGGTCTGG
CAACACAGCGACTCTGACCATCAGCTCGCTCCAGGCTGAGGACGAGGCCGAT
TATTACTGTTCATCTTACGACAGTAGTCACTATAGTATTTTCGGCAGTGGGAC
CAGCCTGACCGTCCTGGGTCAGCCCGCGGCCGCTGGTGGAGGCGGTTCAGGC
GGAGGTGGCTCTGGCGGTGGCGGATCGGCGCGCCAGGTGGAGCTGCAGGAG
TCGGGACCCAGCCTGGTGAAGCCCTCACAGACCCTCTCCCTCACCTGCACGG
TCTCTGGATTCTCATTAAGTAGCAATGCTGTAGGCTGGGTCCGCCAGGCTCCA
GGAAAGGCGCCGGAGTGGGTTGGTGGTATAGATATAGATGGAAGGCCGGTCT
ATAAACCAGGCCTTAAGTCCCGGCTCAGCATCACCAGGGACACCTCCAACGC
TCAAGTCTCCCTGTCACTGAGCAGCGTGACAACTGAGGACACGGCCGTGTAC
TTCTGTGCAAGTTATTATGGTGGTTATCTTTATAATTATGCCCCTGGGGCATAT
ATCGAGCACTTGAGCCCAGGACTCCTGATCACCGTCTCCTCAACTAGTGGTGC
GCCGGTGCCGTATCCGGATCCGCTGGAAACCGCGTGCCGCA (SEQ ID NO:3)

Fig. 1A

>scFv#7
TCCTATGAACTGACCCAGCCGCCTTCAATGTCGGTGGCCTTGGGACAGACGG
CCAAGGTCACCTGCCAGGGAGACAACTTAGAAAACTTTTATGTTCAGTGGCA
CCAGCAGAAGCCGGGCCAGGCCCCTGTGACGGTCATTTTTCAGGATAATAAG
AGGCCCTCGGGGATCCCTGACCGGTTCTCTGGCTCCAACTCGGGGAACACGG
CCACCCTGACCATCAGCGGGGCCCGGACCGAGGACGAGGCCGACTATTACTG
TCAGTCAGGCCACAGCAGTATCGGTGGTGTTTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCCAGGTGCAGCTGCAGGAGTCGGGACC
CAGCCTGGTGAAGCCCTCACAGACCCTCTCCCTCACCTGCACGGTCTCTGGCT
TCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACG
GCCCTGAAGTCCCGGCTCAGCATCACCAGGGACACCTCCAAGAGGCAAGTCT
CCCTATCACTGAGCAGCGTGACGACTGAGGACACGGCCATGTACTTCTGTGC
AAGATCGGCATATAGTACTCTTTATGATTATGAGTATGCCGCTGATATCTACG
ACTGGGGCCCAGGACTCCTGGTCACCGTCTCCTCAACTAGTGGTGCGCCGGT
GCCGTATCCGGATCCGCTGGAACCGCGTGCCGCA (SEQ ID NO:5)

>scFv#8
TCCTATGAACTGACCCAGCCGCCTTCAGTGTCGGTGGTTTGGGGNCNGANGG
CCGAGATCACCTGCCAGGGAGACCTACTGGATAAAAAATATACAGCTTGGTA
CCAGCAGAAGCCGGGCCAGGCTCCTATGAAAATCATTAATAAAGACAGTGAG
CGGCCTTCAGGGATCCGGGACCGGTTCTCGGGCTCCAGCTCAGGCAAAACAG
CCACCCTAACCATCAACGGGGCCCGGCCTGAGGACGAGGCCGACTATTACTG
TTTATCAGGTGACAGCAATAATAATGGTGTCTTCGGCAGCGGGACCAGCCTG
ACCGTCCTGGGTCAGCCCGCGGCCGCTGGTGGAGGCGGTTCAGGCGGAGGTG
GCTCTGGCGGTGGCGGATCGGCGCGCCAGGTGGAGCTGCAGGGGTCGGGAC
CCAGCCTGGTGAAGCCCTCGCAGACCCTCTCCCTCACCTGCACGGTCTCTGGA
TTCTCATGGCCCAACAATGCTGTGGATTGGGTCCGCCAGGCTCCAGGAAAGG
CGCCGGAGTGGCTTGGTGGTATTGCCGATAATGGAAGAACAAACTACAACAC
GGCCCTAAAAGCCCGGCTCAGCATCACTAGGGACACCGCCAAGAGCCATGTC
TCCCTATCGCTGAGCAGCGTGACAGCTGAGGATACGGCCGTTTACTATTGTAC
AGCGGGGGTTATGGTCATGCACGCCACTGACTACTGGGGCCCGGGACTCCTG
GTCACCGTCTCCTCAACTAGTGGTGCGCCGGTGCCGTATCCGGATCCGCTGGA
ACCGCGTGCCGCA (SEQ ID NO:7)

Fig. 1B

>scFv#21
CAGGCTGTGGTGACTCAGCCGTCCTCCGTGTCCGGGTCCCCGGGCCNNANAG
TCTCCATCACCTGCTCTGGAAGCAGCAGCAACGTTGGTAGATATGCTGTAGG
CTGGTTCCAACAGCTCCCAGGATCGGGCCTCAGAACCGTCATCTATTATAATA
GCAATCGACCCTCAGGGGTCCCCGACCGATTCTCTGGCTCCAAATCGGGCAA
CACAGCCACCCTGACCATCAGCTCGCTCCAGGCTGAGGATGAGGCCGATTAT
TTCTGTGGAAGTTATGACAGTAGTATCTATGGTGTTTTCGGCAGCGGGACCAG
GCTGACCGTCCTGGGTCAGCCCGCGGCCGCTGGTGGAGGCGGTTCAGGCGGA
GGTGGCTCTGGCGGTGGCGGATCGGCGCGCCAGGTGCAGCTGCAGGAGTCGG
GACCCAGCCTGGTGAGGCCCTCACAGACCCTCTCCCTCACCTGCACGATCTCT
GGATTCTCTTTAAGAGAGTATGGTGTAGGTTGGGTCCGCCAGGCTCCAGGAA
AGGCGTTGGAGTGGCTTGGGCGAATAGATGATTCTGGATACACATTACATAA
TCCTGCCCTTAAGTCCCGGCTCACCATAACTAGGGACATCTCCAAGAGCCAA
GTCTCCCTGTCACTGAGCAGCGTGACACTTGAGGACACGGCCGAATATTACT
GCGTATATGCTAGTCGTGGTACTGCTTGGTTGGGAGACATCGATGTCTGGGGC
CCAGGACTCCTGCTCACTGTCTCCTCAACTAGTGGTGCGCCGGTGCCGTATCC
GGATCCGCTGGAACCGCGTGCCGCA (SEQ ID NO:9)

>scFv#E
CAGGCTGTGCTGACTCAGCCGTCCTCCGTGTCCAGGTCCCTGGGCCNNANTGT
CTCGATCACCTGCTCTGGAGGCAGCAGCAACGTTGGACAAGGTGATTATGTG
GCCTGGTTCCAACAGGTCCCAGGATCAGCCCCCAAACTCCTCATCTATGATGC
GACGAATCGAGCCTCGGGGGTCCCCGACCGATTCGTCGGCTCCAGATATGGC
AACTCAGCGACTCTGATCATCACCTCGGTCCAGGCTGAGGACGAGGCCGATT
ATTATTGTGCATCTTATGACAGTAGTATGTATACGATTTTCGGCAGCGGGACC
AGCCTGACCGTCCTGGGTCAGCCCGCGGCCGCTGGTGGAGGCGGTTCAGGCG
GAGGTGGCTCTGGCGGTGGCGGATCGGCGCGCCAGGTGGAGCTGCAGGGGTC
GGGACCCAGCCAGGTGAAGCCCTCACAGACCCTCTCCCTCATCTGCACGATC
TCTGGATTCTCATTAACCAGCAATAATGTAGCCTGGGTCCGCCAGGCTCCAGG
AAAGGGACTGGAGTGGGTTGGTGTCATAAGTGATGGTGGAACTCCATACTAT
AACTCGGCCCTGAAATCCCGGCTCAGCATCACCAGGGACACCTCCAAGAGCC
AGGTCTCCCTGTCACTGAGCAGCGTGACAACTGAGGACACGGCCGTGTACTA
CTGTGCACGGACGTTGGATTATAGTCATATTTGGTTGTACTCCGCCGACCAAT
GGGGCCCAGGACTCCTGGTCACCGTCTCCTCAACTAGTGGTGCGCCGGTGCC
GTATCCGGATCCGCTGGAACCGCGTGCCGCA (SEQ ID NO:11)

Fig. 1C

Anti-BoNT/A sheep scFv amino acid sequences

>scFv#2
QAVLTQPSSVSGSPGXXVSITCSGSRSNVGTYGVGWFQQLPGSGLRTIIYYNDKR
PSGVPDRFSASKSGNTATLIISSLQAEDEADYFCGSADGSSYGIFGSGTRLTVLGQ
PAAAGGGGSGGGGSGGGGSARQVGLQESGPSLVKPSQTLSLTCTVSGFSLSNSV
VGWVRQAPGKVPEWLGSIDSGGYTVADPALKSRLSITRDTSKSQVSLSLNSVTTE
DTAVYYCTRAYSITYYAYPPYIDYWGPGLLVTVSSTSGAPVPYPDPLEPRAA
(SEQ ID NO:2)

>scFv#3
QAVLTQPSSVSRSLGQSVSITCSGSSSNVGYGDYVGWFQRVPGSAPKLLIYGATT
RASGVPDRFSGSRSGNTATLTISSLQAEDEADYYCSSYDSSHYSIFGSGTSLTVLG
QPAAAGGGGSGGGGSGGGGSARQVELQESGPSLVKPSQTLSLTCTVSGFSLSSN
AVGWVRQAPGKAPEWVGGIDIDGRPVYKPGLKSRLSITRDTSNAQVSLSLSSVTT
EDTAVYFCASYYGGYLYNYAPGAYIEHLSPGLLITVSSTSGAPVPYPDPLEPRAA
(SEQ ID NO:4)

>scFv#7
SYELTQPPSMSVALGQTAKVTCQGDNLENFYVQWHQQKPGQAPVTVIFQDNKR
PSGIPDRFSGSNSGNTATLTISGARTEDEADYYCQSGHSSIGGVFGSGTSLTVLGQ
PAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTE
DTAMYFCARSAYSTLYDYEYAADIYDWGPGLLVTVSSTSGAPVPYPDPLEPRAA
(SEQ ID NO:6)

>scFv#8
SYELTQPPSVSVVWGXXAEITCQGDLLDKKYTAWYQQKPGQAPMKIINKDSERP
SGIRDRFSGSSSGKTATLTINGARPEDEADYYCLSGDSNNNGVFGSGTSLTVLGQ
PAAAGGGGSGGGGSGGGGSARQVELQGSGPSLVKPSQTLSLTCTVSGFSWPNNA
VDWVRQAPGKAPEWLGGIADNGRTNYNTALKARLSITRDTAKSHVSLSLSSVTA
EDTAVYYCTAGVMVMHATDYWGPGLLVTVSSTSGAPVPYPDPLEPRAA
(SEQ ID NO:8)

>scFv#21
QAVVTQPSSVSGSPGXXVSITCSGSSSNVGRYAVGWFQQLPGSGLRTVIYYNSNR
PSGVPDRFSGSKSGNTATLTISSLQAEDEADYFCGSYDSSIYGVFGSGTRLTVLGQ
PAAAGGGGSGGGGSGGGGSARQVQLQESGPSLVRPSQTLSLTCTISGFSLREYGV
GWVRQAPGKALEWLGRIDDSGYTLHNPALKSRLTITRDISKSQVSLSLSSVTLED
TAEYYCVYASRGTAWLGDIDVWGPGLLLTVSSTSGAPVPYPDPLEPRAA (SEQ
ID NO:10)

Fig. 1D

>scFv#E
QAVLTQPSSVSRSLGXXVSITCSGGSSNVGQGDYVAWFQQVPGSAPKLLIYDAT
NRASGVPDRFVGSRYGNSATLIITSVQAEDEADYYCASYDSSMYTIFGSGTSLTV
LGQPAAAGGGGSGGGGSGGGGSARQVELQGSGPSQVKPSQTLSLICTISGFSLTS
NNVAWVRQAPGKGLEWVGVISDGGTPYYNSALKSRLSITRDTSKSQVSLSLSSV
TTEDTAVYYCARTLDYSHIWLYSADQWGPGLLVTVSSTSGAPVPYPDPLEPRAA
(SEQ ID NO:12)

Fig. 1E

Nucleic acid sequence of scFv#7-2E is:

GGTGCGCCGGTGCCGTATCCGGATCCGCTCGAGCCGCGTGCCGGCTCCTATGAACTG
ACCCAGCCGCCTTCAATGTCGGTGGCCTTGGGACAGACGGCCAAGGTCACCTGCCAG
GGAGACAACTTAGAAAACTTTTATGTTCAGTGGCACCAGCAGAAGCCGGGCCAGGC
CCCTGTGACGGTCATTTTTCAGGATAATAAGAGGCCCTCGGGGATCCCTGACCGGTT
CTCTGGCTCCAACTCGGGGAACACGGCCACCCTGACCATCAGCGGGGCCCGGACCG
AGGACGAGGCCGACTATTACTGTCAGTCAGGCCACAGCAGTATCGGTGGTGTTTTCG
GCAGCGGGACCAGCCTGACCGTCCTGGGTCAGCCCGCGGCCGCTGGTGGAGGCGGT
TCAGGCGGAGGTGGCTCTGGCGGTGGCGGATCGGCGCGCCAGGTGCAGCTGCAGGA
GTCGGGACCCAGCCTGGTGAAGCCCTCACAGACCCTCTCCCTCACCTGCACGGTCTC
TGGCTTCTCATTAACGGGAAATTCTGTAACCTGGGTCCGCCAGGCTCCAGGAAACGT
GCCGGAGTGGCTTGGTGGTATAAGCCGCGGTGGACGCACATACTATGATACGGCCCT
GAAGTCCCGGCTCAGCATCACCAGGGACACCTCCAAGAGGCAAGTCTCCCTATCACT
GAGCAGCGTGACGACTGAGGACACGGCCATGTACTTCTGTGCAAGATCGGCATATA
GTACTCTTTATGATTATGAGTATGCCGCTGATATCTACGACTGGGGCCCAGGACTCC
TGGTCACCGTCTCCTCAACTAGTGGTGCGCCGGTGCCGTATCCGGATCCGCTGGAAC
CGCGTGCCGCA (SEQ ID NO: 13)

Amino acid sequence of scFv#7-2E is:

GAPVPYPDPLEPRAGSYELTQPPSMSVALGQTAKVTCQGDNLENFYVQWHQQKPGQAP
VTVIFQDNKRPSGIPDRFSGSNSGNTATLTISGARTEDEADYYCQSGHSSIGGVFGSGTSL
TVLGQPAAAGGGGSGGGGSGGGGSARQVQLQESGPSLVKPSQTLSLTCTVSGFSLTGNS
VTWVRQAPGNVPEWLGGISRGGRTYYDTALKSRLSITRDTSKRQVSLSLSSVTTEDTAM
YFCARSAYSTLYDYEYAADIYDWGPGLLVTVSSTSGAPVPYPDPLEPRAA
(SEQ ID NO:14)

Fig. 2

METHODS AND SYSTEMS FOR MULTI-ANTIBODY THERAPIES

RELATED APPLICATION

This application claims the benefit of U.S. Provisional Application No. 60/890,626, filed Feb. 20, 2007.

GOVERNMENT SUPPORT

This invention was made with government support under grant AI030050 awarded by the National Institutes of Health. The government has certain rights in the invention.

The entire teachings of the above application are incorporated herein by reference.

BACKGROUND OF THE INVENTION

The production of antibodies and their storage is often a costly and lengthy process. In fact, development of a single antibody therapeutic agent can take years. Yet the use of multiple, different therapeutic antibodies are often necessary or desirable for the effective treatment of patients following a disease, outbreak or a bio-terrorist assault. The threat of a pandemic attack is real, and efforts to stockpile agents to combat such an outbreak have been attempted. However, producing and stockpiling enough antibody to protect large populations is challenging. The shelf life of antibodies is often relatively short, and so antibodies have to be periodically replaced. As a result, developing and producing multiple antibodies that can bind to different targets (e.g. microbial and viral pathogens, toxins, cancer cells) for improved therapeutic effect is often a difficult task because it involves storing multiple antibodies for each pathogen or toxin.

Hence, a need exists for a cost effective and efficient way to provide antibody treatments to a large quantity of people. A further need exists for antibody therapeutics that are easier to develop and produce, and have a longer shelf life. Yet, a further need exists for antibody therapeutics that bind to multiple targets on the same disease agent, as well as different disease agents.

SUMMARY OF THE INVENTION

The methods of the present invention include methods for administering antibody therapeutic agents to treat one or more disease agents. The steps involve administering at least one binding agent, wherein the binding agent has a binding region and one or more copies of a tag; and administering an anti-tag antibody (e.g., an anti-tag antibody), wherein the anti-tag antibody has an anti-tag region that is specific to the tag (e.g., to the one or more tags). The binding region of the binding agent is specific to a portion of the disease agent. The binding agent binds to a portion of the disease agent (e.g., the target) and the anti-tag antibody binds to the tag of the binding agent. Accordingly, the anti-tag antibody, which is directed to the disease agent by the binding agent, provides the effector activity that leads to a therapeutic effect. In fact, anti-tag antibody further embodies a polyclonal, antibody mixture, or an immunoglobulin such as IgA, IgD, IgE, IgG, or IgM. An embodiment of the methods includes administering two or more binding agents, each having a binding region that binds to different portions of the disease agent, but each have the same tag or multiple copies of the same tag. The binding region of the binding agent can be an antibody fragment, a microprotein, peptide, a synthetic molecule, or an aptamer. The disease agent, in an embodiment, can be a virus, bacteria, cancer cell, parasite, or a molecule, protein or toxin produced therefrom. The tag can be an antibody epitope, including a polypeptide, sugar or DNA molecule. In the case of a polypeptide, the tag encompasses the epitope and generally includes between about 8 to about 15 amino acids (e.g., having an amino acid sequence of SEQ ID NO: 15).

The methods of the present invention further include methods of treating an individual having a viral infection, parasitic infection, bacterial infection, cancer, or a molecule, protein or toxin produced therefrom (e.g., a pathogenic molecule, protein, or toxin). The method relates to administering at least one binding agent, as described herein, and administering an anti-tag antibody, also as described herein. The administration of the binding agent and the anti-tag antibody can occur at the same time or at different times (e.g., sequentially). The methods include reducing one or more symptoms associated with the viral infection, parasitic infection, bacterial infection, cancer or protein or toxin produced therefrom.

The present invention further embodies an antibody therapeutic system or kit that has at least one binding agent, and an anti-tag antibody, described herein.

Lastly, the present invention pertains to isolated polypeptide and nucleic acid molecules relating to the binding agents specific to a botulism neurotoxin disease agent. Specifically, the present invention includes binding agents with amino acid sequence encoded by a nucleic acid molecule having a sequence of SEQ ID NO: 1, 3, 5, 7, 9, 11, 13 or combination thereof an amino acid sequence encoded by a complement of SEQ ID NO: 1, 3, 5, 7, 9, 11, 13, or combination thereof an amino acid sequence encoded by a nucleic acid molecule that hybridizes to SEQ ID NO: 1, 3, 5, 7, 9, 11, 13, or combination thereof and an amino acid sequence set forth in SEQ ID NO: 2, 4, 6, 8, 10, 12, 14, or combination thereof. Similarly, the present invention includes nucleic acid molecules having one of the following sequences: SEQ ID NO: 1, 3, 5, 7, 9, 11, 13, or combination thereof a complement of SEQ ID NO: 1, 3, 5, 7, 9, 11, 13, or combination thereof that hybridizes to SEQ ID NO:1, 3, 5, 7, 9, 11, 13, or combination thereof and that encodes SEQ ID NO: 2, 4, 6, 8, 10, 12, 13, or combination thereof. The present invention further includes binding agents having one or more copies of a tag with an amino acid sequence of SEQ ID NO: 15. Vectors, plasmids, or host cells having the nucleic acid molecules or that express the amino acid molecules of the present invention are further included herein. The present invention includes compositions that have the binding agents and an anti-tag antibody of the present invention and a physiologically acceptable carrier.

The present invention has a number of advantages. The systems and methods of the present invention allow for a more efficient system of treating disease agents and for storing quantities of antibodies for a large number of people. Binding agents of the present invention are compositions that can be stored for a longer period of time, as compared to antibodies with heavy and light chains. Binding agents are also generally easier to make than antibodies. The invention involves multiple (e.g., two or more) binding agents for use against multiple targets of the same disease, which often results in greater effectiveness. The binding agents in the system have the same tag, and an anti-tag antibody binds to all of the binding agents, even those that are specific to different portions of the disease agent. To make and store multiple antibodies for a number of targets is costly and inefficient, in comparison. Hence, a number of binding agents can more easily be stored, e.g., to protect against a potential biological threat, along with a single anti-tag antibody.

BRIEF DESCRIPTION OF THE DRAWINGS

FIGS. 1A-E show the nucleic acid sequences of scFv#2 (SEQ ID NO: 1), scFv#3 (SEQ ID NO: 3), scFv#7 (SEQ ID NO: 5), scFv#8 (SEQ ID NO: 7), scFv#21 (SEQ ID NO: 9), scFv#E (SEQ ID NO: 11), and amino acid sequences of scFv#2 (SEQ ID NO: 2), scFv#3 (SEQ ID NO: 4), scFv#7 (SEQ ID NO: 6), scFv#8 (SEQ ID NO: 8), scFv#21 (SEQ ID NO: 10), scFv#E (SEQ ID NO: 12).

FIG. 2 shows the nucleic acid sequence of scFv#7-2E (SEQ ID NO: 13) and amino acid sequence of scFv#7-2E (SEQ ID NO: 14).

DETAILED DESCRIPTION OF THE INVENTION

The present invention relates to methods and systems that include one or more binding agents having a binding region and an epitopic tag; and an anti-tag antibody that binds the tag. The anti-tag antibody has a tag-specific binding region, also referred to as "anti-tag region." The methods of the present invention use, in an embodiment, two or more binding agents that are specific for different targets of the same disease agent, but have the same epitopic tag. Since the anti-tag antibody is specific for the tag, it can bind to each of the different binding agents. Additionally, in certain instances in which a single binding agent has more than one copy of the same tag, the overall efficacy of the antibody therapy increases.

Accordingly, in vivo, the binding agents bind to the disease agent (e.g., a polypeptide toxin produced by a bacterium). Using two or more binding agents has shown to be particularly effective in ridding the subject of the disease agent and improving symptoms caused by it. See Exemplification. The anti-tag antibody then binds to all of the binding agents, even binding agents that are specific for different portions of the disease agent. In the case in which the binding agents have multiple, identical tags, the anti-tag antibody has more available sites to which it can bind. As such, the anti-tag antibody allows for effector functions to occur (e.g., phagocytosis, neutralization, clearance of the disease agent), and in certain instances, an increase in the effector functions occurs when more than one copy of the tag is present on the binding agent. Binding agents are generally easier to make and have longer shelf-lives than antibodies. Rather than having multiple antibodies, which are more difficult to engineer and store, multiple binding agents along with a single anti-tag antibody can be used to treat individuals.

Binding Agent

The binding agent is a molecule that binds to a portion of a disease agent, and has a tag. The antibody therapeutic agents of the present invention allow the disease agent to be cleared, undergo phagocytosis, undergo neutralization, be inhibited, or otherwise mitigated by immune activity.

Binding agents include molecules such as antibody fragments (e.g., single chain antibodies, and nanobodies), microproteins (also referred to as cysteine knot proteins or knottins), darpins, anticalins, adnectins, peptide mimetic molecules, aptamers, synthetic molecules, and any molecule that binds to a disease agent and can elicit immune effector activity against the disease agent when the binding agent is bound by an anti-tag antibody. The binding agent, along with the anti-tag antibody, results in various effector functions such as phagocytosis and/or clearance, which is further described herein.

In certain embodiments, the binding agents can neutralize or inhibit the disease agent. In the case that the binding agents themselves are neutralizing, they can be advantageous in that they neutralize at the same time as triggering antibody mediated effector activity. In an example, a binding agent, referred to as scFvs (#2) in the Exemplification, is a neutralizing agent and it works well, as compared to similar neutralizing agents. However, in certain experiments performed in the exemplification, a neutralizing binding agent is not always necessary to protect mice from the toxin. Additionally, another factor is that the anti-tag antibody can increase the serum half-life of the binding agents.

Binding Agents that Include Antibodies Fragments, Microproteins and Other Molecules that Bind the Disease Agent The term "antibody fragment" refers to portion of an immunoglobulin having specificity to the disease agent, or a molecule involved in the interaction or binding of the disease agent. The term, "antibody fragment", is intended to encompass fragments from both polyclonal and monoclonal antibodies including transgenically produced antibodies, single-chain antibodies (scFvs), recombinant Fabs, and recombinant camelid heavy-chain-only antibodies (VHHs). VHHs are also referred to as nanobodies.

Nanobodies are antibody-derived therapeutic proteins that contain the unique structural and functional properties of naturally-occurring heavy-chain antibodies. The Nanobody technology is based on fully functional antibodies from camelids that lack light chains. These heavy-chain antibodies contain a single variable domain (VHH) and two constant domains (CH2 and CH3). The cloned and isolated VHH domain is a stable polypeptide harboring the antigen-binding capacity of the original heavy-chain antibody. (Ablynx, Ghent, Belgium; http://www.ablynx.com/02_understanding.htm.)

Suitable methods of producing or isolating antibody fragments of the requisite specificity are known in the art and include for example, methods which select recombinant antibody from a library, by PCR.

Functional fragments of antibodies, including fragments of chimeric, humanized, primatized, veneered or single chain antibodies, can also be produced. Functional fragments or portions of the foregoing antibodies include those which are reactive with the disease agent. For example, antibody fragments capable of binding to the disease agent or portion thereof, including, but not limited to scFvs, Fabs, VHHs, Fv, Fab, Fab' and F(ab')$_2$ are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain. Accordingly, the present invention encompasses a polynucleic acid that encodes the binding agent described herein (e.g., a binding fragment with a tag).

Antagonist includes proteins or polypeptides that bind to the disease agent, inhibit function of the disease agent, and can form the binding region of the binding agent. Known antagonists, or those developed in the future, can be used with the present invention.

Binding agents include any molecule that binds to the disease agent including those that have scaffolds. Other examples of molecules include DARPins, Anticalins, and AdNectins. DARPins are derived from natural ankyrin repeat proteins and bind to proteins including e.g., human receptors, cytokines, kinases, human proteases, viruses and membrane proteins (Molecular Partners AG Zurich Switzerland). Anticalins are derived from lipocalins, and comprise a hypervariable loops supported by a conserved β-sheet framework, which acts as a binding agent. (Pieris AG, Germany). The scaffold for anticalins are lipocalins. AdNectins are derived from human fibronectin (e.g., the scaffold), and bind to targets of various medical conditions. (Adnexus, Waltham Mass.).

Binding Agent for Botulinum neurotoxin (BoNT) serotype A (BoNT/A)

In particular, the present invention relates to binding agents that are specific to the microbial neurotoxin that causes botulism. There are at least seven different botulinum toxin serotypes (A to G), sometimes with various isotypes, and many of these different toxins can cause human disease. As described in the Exemplification section, several binding agents specific to one of the botulinum neurotoxins, serotype A (BoNT/A) were made. Hence, the methods and systems of the present invention include binding agents that have binding regions specific to one or more target areas of one or more neurotoxins involved with botulism. Sequences engineered to bind to this neurotoxin are shown in FIG. 1. Specifically, the present invention relates to binding agents having the amino acid sequence of SEQ ID NO: 2, 4, 6, 8, 10, 12, 14, or combination thereof. Similarly, the present invention also includes binding agents that are encoded by a nucleic acid sequence of SEQ ID NO: 1, 3, 5, 7, 9, 11, 13, or combination thereof. A tag was engineered and has amino acid sequence of SEQ ID NO: 15, and is genetically fused to the carboxyl end of these binding agents.

The present invention embodies multiple binding agents, each to target different areas of one or more disease agents. In an embodiment, two or three binding agents specific to different targets of a disease agent can be used. In a case in which a number of disease agents can be involved in causing a disease or condition, such as botulism, multiple disease agents can be targeted. In the case of botulism, since any one of at least seven neurotoxin serotypes could be responsible, a pool of binding agents can be prepared that contain binding agents for all of the known serotypes that cause human disease. Botulism is often caused by exposure to a single BoNT serotype, but it is generally difficult to quickly determine which serotype is the cause. Thus, the standard of care in treating botulism includes administration of a number of antibodies to protect against most if not all of the serotypes that cause the disease in human. Hence, to protect against such a disease, an embodiment includes having or stockpiling binding agents that bind to several or preferably all of the serotypes that cause botulism. Certain studies have shown that effective antibody neutralization of a single BoNT serotype requires three different anti-BoNT monoclonal antibodies. Thus, to protect patients against all seven BoNT serotypes would require a pool of 21 different mAbs, a very formidable task. In contrast, preparation of a pool of small binding agents, each with a common tag, together with a single anti-tag mAb is a much more achievable task.

Similarly, the targeted disease agents can be agents from different classes of pathogens. For example, a multi-target approach further includes binding agents that bind to viral disease agents, bacterial disease agents, parasite disease agents, cancer cells, proteins produced therefrom and any combination therefrom.

Tags of Binding Agents

The binding agent is modified, for example, by incorporation of or attachment (directly or indirectly (e.g., via a linker)) of one or more tags. A tag is a molecule or antibody epitope that is attached or genetically fused to the binding agent and to which the anti-tag antibody binds. Genetic fusion refers to a recombinant protein that is engineered to contain extra amino acid sequences that constitute the tag. Thus, the DNA encoding the tag is joined (in reading frame) with the DNA encoding the binding agent. An embodiment of the invention includes more than one binding agents, with the same tag. Hence, in a system, the anti-tag antibody binds to all of the binding agents via the tag.

The tag can be attached to a portion of the binding agent so long as the tag does not interfere with the agent's ability to bind to the disease agent. The tag, for example, can be a polypeptide, sugar, or DNA molecule.

In an embodiment, the tag is incorporated by genetic fusion at the carboxyl end of the binding agent. The tag, itself, can also be a polypeptide joined at the amino terminal end or within the binding agent as long as the tag does not affect binding of the binding agent to the target and the tag remains accessible to the anti-tag mAb. The tag itself does not interact or bind with the disease agent. Preferably, the tag is an uncommon or unique molecule or peptide in nature. In an aspect, the tag is a polyptepide that ranges from about 5 amino acids to about 20 amino acids, and preferably between about 8 and about 15. In the exemplification, the tag used consisted of the following 13 amino acids: GAPVPYPDPLEPR (SEQ ID NO: 15). Examples of such tags also include c-myc and haemagglutinin protein, biotin, avidin, hapten (e.g., a carbohydrate or nucleotide) and the like.

The tag can be incorporated into the binding agent using recombinant technology in which the DNA encodes the binding agent genetically fused with the tag. Specifically, the coding sequence for the tag can be cloned into an expression vector and transfected into cells for recombinant expression.

Once the tag is incorporated into the binding agent, the binding agent, like an antibody, can be evaluated for its ability and affinity to bind to the disease agent.

Optionally, a linker or spacer can be used to attach the binding region of the binding agent with the tag. A linker can be used to indirectly attach a tag to the binding region. In one embodiment of the invention, the binding agent includes the binding region, a linker and a tag. The spacer/linker can be any compound, now known or later developed, that can attach the binding region with the tag.

Inclusion of more than one copy of the tag on a binding agent, in certain aspects, has additional advantages, such as by increasing the number of anti-tag antibodies that can bind to the binding agent. This would be the case, for example, where increasing the number of antibody Fc effector domains bound to the pathogenic protein through the tagged binding agent increased the therapeutic efficacy. Such an increase in efficacy is demonstrated and described in the Exemplification.

Disease Agent

The disease agent to which the binding agent binds can be any disease-causing target including those to be inhibited, or whose activity can be altered (e.g., neutralized, reduced or ceased), or that can be recognized by immune effectors and lead to clearance, opsonization, killing, etc. The disease agent can be a portion of a pathogen or a molecule released or secreted by the pathogen (e.g. toxin). A pathogen is an agent that causes a disease or condition, and includes a virus, cancer cell, bacterium, parasite or pathogenic protein. The disease agents include pathogenic proteins that are derived from normal cells, such as prions. Proteins or other molecules that are disease agents can be either independent of the pathogen or associated with or produced by a pathogen.

A virus is a microscopic particle that can infect the cells of a biological organism and replicate themselves in the host cell. With respect to the present invention, viral antigens, usually proteins, are targeted by the binding agent. Binding agents can be made to bind to such molecules on the virus, using the processes described herein. Example of viruses include Influenza, Rhinovirus, Rubeola, Rubella, Herpes, Smallpox, Chickenpox, Human Papilloma, Rabies, and Human Immunodeficiency viruses.

A parasite is an organism which lives on or in a different organism. Parasites have or express molecules that can be used as a target by the binding agent. Types of parasites include endoparasites (e.g., parasites that live inside the body of the host) and ectoparasites (e.g., parasites that live on the outside of the host's body). Examples of parasites include protozoans (e.g., plasmodium, cryptosporidium, microsporidia, and isospora), ticks, lice and parasitic worms.

Molecules on cancer cells can also be targets of the binding agent. In one embodiment, the target is a protein on the cancer cell or proteins that are characteristic to the cells of the cancer in question. Examples of proteins associated with cancer cells include CD33 (i.e., to a cytotoxic agent expressed in most leukemic blast cells), and the HER2/neu receptor for breast cancer.

Bacteria that can also be a target for the present invention include any bacteria including gram negative and gram positive bacteria. Examples of pathogenic bacteria belong to the genuses such as *Clostridium, Staphylococcus, Neisseria, Streptococcus, Moraxella, Listeria,* Enterobacteriaceae, *Escherichia coli, Corynebacterium, Klebsiella, Salmonella, Shigella, Proteus, Pseudomonas, Haemophilus, Bordetella, Legionella, Campylobacter, Helicobacter,* and *Bacteroides.* Methods for ascertaining the target are known in the art and will depend on the type of molecule being inhibited. For example, in the case where a class or group of bacteria are to be inhibited, conserved regions of a bacteria can be targeted, and binding agents that bind to these targets can be made. In other cases, if a specific bacterium is to be inhibited, then a non-conserved region of the bacteria can be targeted with the binding agents. The binding of the agents can be measured using standard assays, such as ELISAs, western blots and radioimmunoassays.

Pathogenic molecules including polypeptides or toxins are also disease agents to which binding agents can target. Pathogenic proteins refers to proteins that can cause, directly or indirectly, a disease, or condition in an individual. Proteins or toxins produced by bacteria, virus, or cancer cells are often such examples. In the Exemplification section, binding agents were made to a toxin produced by a *Clostridium bacterium.*

As shown in the Exemplification, using binding agents that target more than one area of the disease agent are shown more effective at protecting animals from the pathology of the disease agent, and symptoms caused by the disease agent are reduced or alleviated all together, as further described herein.

Anti-Tag Antibody

The anti-tag antibody is, in an embodiment, an antibody having an anti-tag region. The anti-tag region of the anti-tag antibody binds to the tag of each of the binding agents. Since the same tag is used for each of the binding agents, the anti-tag antibody essentially binds to the binding agents via the tag.

To generate an anti-tag antibody, processes known for making monoclonal antibodies, which are described herein, can be used. In the process of making monoclonal antibodies, for example, a mouse is injected with a disease agent along with an adjuvant. After a series of injections, the spleen of the mouse is removed, and the cells that make the antibody are fused with myeloma SP2/0 cells. The fused cells are grown and tested for their ability to make an antibody that binds to the disease agent, e.g., with ELISAs. To elicit an antibody that is specific to the tag, the tag, rather than the disease agent, is injected into the mouse during this process. Since the tags are generally small molecules (e.g. haptens) or peptides, they may need to be chemically coupled to a larger antigen for immunization or, if peptides, expressed as a genetic fusion to a larger protein, to make them more immunogenic. Humanized or chimeric antibodies can be made once the variable regions are determined.

Antibodies are already described herein, and can be used to carry out or facilitate effector functions. The anti-tag antibody further includes an immunoglobulin such as IgA, IgD, IgE, IgG, and IgM, including subtypes thereof. In addition to monoclonal antibodies, polyclonal antibodies specific to the tag can also be used with the present invention. Effector functions are generally carried out by the Fc portion of the immunoglobulin. Depending on the type of immunoglobulin chosen, the effector functions results in clearance of the disease agent (e.g., excretion, degradation, lysis or phagocytosis). Other molecules, now known or developed in the future, can be used as an anti-tag antibody so long as they bind to the tag and contain one or more of the antibody effector functions. For example, an anti-tag antibody may be an engineered protein consisting only of a domain that binds to the tag (e.g. an anti-tag scFv or VHH) fused to a minimal functional antibody Fc domain.

In mammals there are at least five types of antibody: IgA, IgD, IgE, IgG, and IgM, with 4 IgG and 2 IgA subtypes present in humans. These are classified according to differences in their heavy chain constant domains. Each immunoglobulin class differs in its biological properties. IgA can be found in areas containing mucus (e.g. in the gut, in the respiratory tract or in the urogenital tract) and prevents the colonization of mucosal areas by pathogens. IgD functions mainly as a disease agent receptor on B cells. IgE binds to allergens and triggers histamine release from mast cells and also provides protection against helminths (worms). IgG, in its four forms, provides the majority of antibody-based immunity against invading pathogens. IgM is expressed on the surface of B cells and also in a secreted form with very high affinity for eliminating pathogens in the early stages of B cell mediated immunity.

Some cells such as mast cells and phagocytes have specific receptors on their cell surface for binding antibodies. These are called Fc receptors and they interact with the Fc region of some antibodies (e.g. IgA, IgG, IgE). The engagement of a particular antibody with the Fc receptor on a particular cell will trigger the effector function of that cell. For example, phagocytes will phagocytose, and mast cells will degranulate. Effector functions generally result in destruction of the invading microbe. Hence, the type of immunoglobulin can be chosen depending on the type of effector function desired.

Methods and Systems of Administering Antibody Therapeutic Agents

The present invention includes methods of administering one or more binding agents and an anti-tag antibody, as described herein, to an individual. The binding agents having a binding region that is specific to the disease agent and one or more tags are administered. The binding agents bind to the target region on the disease agent. Administration of two or more binding agents, in an embodiment, increases the effectiveness of the antibody therapy, and better reduces the severity of one or more symptoms. Similarly, when the binding agents have more than one copy of the tag, an increase in efficacy occurs in certain embodiments. A single anti-tag antibody type binds to all binding agents with the tag. In the case in which the binding agents have multiple copies (e.g., two or more) of the same tag, the anti-tag antibody can bind to each copy of the tag on the binding agent. The phrase, "antibody therapeutic agents" or "antibody therapeutic preparation" refers to one or more compositions that include at least one binding agent and at least one anti-tag antibody, as described herein. The preparation can have additional elements including carriers, as described herein.

The administration of the binding agent and anti-tag antibody can occur simultaneously or sequentially in time. The binding agents can be administered before, after or at the same time as the anti-tag antibody, so long as they are administered close enough in time to have the desired effect (e.g., before the binding agents have been cleared by the body). Thus, the term "co-administration" is used herein to mean that the binding agents and the anti-tag antibody will be administered at times to achieve treatment of the disease, or reduction in the level of the pathogen (e.g., virus, bacteria, cancer cell, proteins associated therewith, or combination thereof) and/or symptoms associated with it. The methods of the present invention are not limited to the sequence in which the binding agents and anti-tag antibody are administered, so long as the compositions are administered close enough in time to produce the desired effect. In an embodiment, the binding agent and anti-tag antibody can be premixed and administered together. The binding agent and anti-tag antibody can also be co-administered with other medications or compositions normally administered when treating the disease agent.

The methods of the present invention include treating a bacterial disease, a parasitic infection, viral diseases, cancer, molecules, proteins or toxins associated therewith. This is accomplished by administering the binding agents and anti-tag antibodies described herein to the infected individual. Administration ameliorates or reduces the severity of one or more the symptoms of the disease or condition. The presence, absence or severity of symptoms can be measured using tests and diagnostic procedures known in the art. Similarly the presence, absence and/or level of the disease agent can be measured using methods known in the art. Symptoms or levels of the disease agent can be measured at one or more time points (e.g., before, during and after treatment, or any combination thereof) during the course of treatment to determine if the treatment is effective. A decrease or no change in the level of the disease agent, or severity of symptoms associated therewith indicates that treatment is working, and an increase in the level of the disease agent, or severity of symptoms indicates that treatment is not working. Symptoms and levels of disease agents are measured using methods known in the art.

For example, where toxin is the disease agent, five mice per treatment group are injected intravenously or intraperitoneally with a lethal dose of toxin (10 LD50, 10× the dose that is lethal to 50% of the mice) and the binding agents to be tested are co-administered. The mice are regularly monitored for symptoms and survival. Symptoms that are monitored include difficulty breathing, lethargy, mobility, appetite and responsiveness. Toxin protection is assessed as increased survival and reduction of symptoms. The steps of the present invention led to a decrease or alleviation of the symptoms, and increase in survival. See Exemplification Section.

The antibody therapeutic agents including one or more binding agents and an anti-tag antibody can be administered in one or more pharmaceutical carriers. The terms "pharmaceutically acceptable carrier" or a "carrier" refer to any generally acceptable excipient or drug delivery device that is relatively inert and non-toxic. The binding agents and anti-tag antibody can be administered with or without a carrier. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The binding agents and anti-tag antibody can be administered systemically or locally (e.g., by injection or diffusion).

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer one or more binding agents and an anti-tag antibody.

The binding agents and anti-tag antibody of the present invention can be administered intravenously, parenterally, orally, nasally, by inhalation, by implant, by injection, or by suppository. The composition can be administered in a single dose or in more than one dose over a period of time to confer the desired effect.

The actual effective amounts of compositions of the present invention can vary according to the binding agent being utilized, the particular composition formulated, the mode of administration and the age, weight and condition of the patient, for example. As used herein, an effective amount of the binding agents and anti-tag antibody is an amount which is capable of reducing one or more symptoms of the disease or conditions caused by the disease agent. Dosages for a particular patient can be determined by one of ordinary skill in the art using conventional considerations, (e.g. by means of an appropriate, conventional pharmacological protocol).

Systems or kits of the present invention include one or more binding agents having a binding region and one or more tags, and an anti-tag antibody having an anti-tag region (e.g., an anti-tag antibody), as described herein.

Polypeptides, Nucleic Acid Sequences, Vectors, Host Cells of the Binding Agents Engineered and Specific to a Botulism Neurotoxin The present invention relates to isolated polypeptide molecules that have been engineered or isolated to act as binding agents. In particular, the present invention includes polypeptide molecules that contain the sequence of any one of the binding agents (SEQ ID NO: 2, 4, 6, 8, 10, 12, 14, or combinations thereof). See FIG. 1. The present invention also pertains to polypeptide molecules that are encoded by nucleic acid sequences, SEQ ID NO: 1, 3, 5, 7, 9, 11, 13, or combinations thereof). A tag having the sequence set forth in SEQ ID NO:15 was used with these sequences.

As used herein, the term "polypeptide" encompasses amino acid chains of any length, including full length proteins (i.e., disease agents), wherein the amino acid residues are linked by covalent peptide bonds. Thus, a polypeptide can comprise a portion of the binding agent, the entire binding agent, or it can contain additional sequences. The polypeptides of the binding agents of the present invention referred to herein as "isolated" are polypeptides that are separated away from other proteins and cellular material of their source of origin. The compositions and methods of the present invention also encompass variants of the above polypeptides and DNA molecules. A polypeptide "variant," as used herein, is a polypeptide that differs from the recited polypeptide only in conservative substitutions and/or modifications, such that the ability of the binding agent to bind to the disease agent target is retained.

The present invention also encompasses proteins and polypeptides, variants thereof, or those having amino acid sequences analogous to the amino acid sequences of binding agents described herein. Such polypeptides are defined herein as analogs (e.g., homologues), or mutants or derivatives. "Analogous" or "homologous" amino acid sequences refer to amino acid sequences with sufficient identity of any one of the amino acid sequences of the present invention so as to possess the biological activity (e.g., the ability to bind to the disease agent target). For example, an analog polypeptide can be produced with "silent" changes in the amino acid sequence wherein one, or more, amino acid residues differ from the amino acid residues of any one of the sequence, yet still possesses the function or biological activity of the polypeptide. In particular, the present invention relates to homologous polypeptide molecules having at least about 70% (e.g., 75%, 80%, 85%, 90% or 95%) identity or similarity with SEQ ID NO: 2, 4, 6, 8, 10, 12, 14 or combination thereof. Percent "identity" refers to the amount of identical nucleotides or amino acids between two nucleotides or amino acid sequences, respectfully. As used herein, "percent similarity" refers to the amount of similar or conservative amino acids between two amino acid sequences.

Homologous polypeptides can be determined using methods known to those of skill in the art. Initial homology searches can be performed at NCBI against the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., Gene, 73:237-244 (1988) e.g., using default parameters).

The present invention, in one embodiment, includes an isolated nucleic acid molecule having a sequence of SEQ ID NO: 1, 3, 5, 7, 9, 11, 13, or combinations thereof. See FIG. 1. As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses isolated nucleic acid sequences that encode the binding agents and in particular, those which encode a polypeptide molecule having an amino acid sequence of SEQ ID NO: 2, 4, 6, 8, 10, 12, 14, or combinations thereof.

As used herein, an "isolated" nucleotide sequence is a sequence that is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences of the binding agents of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the binding agents described herein. In particular, the present invention is directed to nucleic acid molecules having at least about 70% (e.g., 75%, 80%, 85%, 90% or 95%) identity with SEQ ID NO: 1, 3, 5, 7, 9, 11, 13, or combinations thereof.

Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleic acid need not reflect the exact sequence of the sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

The invention also provides vectors, plasmids or viruses containing one or more of the nucleic acid molecules having the sequence of SEQ ID NO:1, 3, 5, 7, 9, 11, 13 or combinations thereof). Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

A description of preferred embodiments of the invention follows.

EXEMPLIFICATION

The concept is to improve therapies that involve multiple monoclonal antibodies (mAbs) by using small recombinant peptide, protein or polynucleotide agents that have the same binding specificity as the mAbs. Each of the recombinant binding agents is produced containing the same epitopic tag. A single mAb that recognizes the epitopic tag is co-administered to patients with the binding agents. The different agents bind to the same targets as the multiple mAbs and the anti-tag mAb binds to these agents through the epitopic tag. This permits delivery of the same therapeutic effect that is achieved with multiple mAb therapy, but requires only a single mAb. If desired, mAbs of different isotypes, or polyclonal anti-tag antibodies, could be used therapeutically to deliver different immune effector activities.

A number of small recombinant protein agents were generated. They were called single-chain Fvs (scFvs) and recognize botulinum neurotoxin serotype A (BoNT/A). These scFvs are essentially recombinant proteins that represent the antigen combining region of an immunoglobulin. Several anti-BoNT/A scFvs were produced and purified at laboratory scale. Each of the scFvs contains the amino acid sequence (GAPVPYPDPLEPR—SEQ ID NO: 15) near the carboxyl terminus which is an epitopic tag referred to herein as "E-tag." One of the scFvs (scFv#2) was shown to neutralize BoNT/A in a cell-based toxin assay (IC50~7 nM). A second scFv (scFv#7) had little or no neutralization activity in the assay, but was found to bind to BoNT/A with high affinity (Kd~1 nM). The scFvs were tested for their ability to protect mice BoNT/A against intoxication following intravenous administration of the agents and toxin. The two scFvs were administered individually or together, and were given +/− a mouse anti-E-tag mAb by intravenous administration. Each mouse received 10 LD50s of BoNT/A, 5 mice per group. The results were as follows:

TABLE 1

Results from Experiment #1

| Agents Administered | Survival | Comments |
| --- | --- | --- |
| None | 0% | Death in less than a day |
| 20 ug scFv#2 | 0% | Death delayed about a day |
| 20 ug scFv#7 | 0% | Death delayed less than a day |
| 20 ug scFv#2 + 25 ug anti-E-tag mAb | 100% | Symptoms severe |
| 20 ug scFv#7 + 25 ug anti-E-tag mAb | 0% | Death delayed several days |
| 10 ug scFv#2 + 10 ug scFv#7 + 25 ug anti-E-tag mAb | 100% | No symptoms |

These results clearly show that a BoNT/A neutralizing scFv (scFv#2) does not significantly protect mice from the toxin unless it is accompanied by a mAb that recognizes an epitopic tag (E-tag) on the scFv. More importantly, combining this mAb with two scFvs, each with E-tag, dramatically improves the protective effect. In this case, the different scFv binding agents provide the additive effect and only the single anti E-tag mAb is needed.

A second study was performed using the same toxin challenge (10 LD50) and lower doses of the scFvs and the anti-E-tag mAb. In addition, two other non-neutralizing anti-BoNT/A scFvs (#3 and #21) were tested in combination with the neutralizing scFv#2. Whether the anti-E-tag mAb would function if administered at a different site and time than the toxin was also tested.

TABLE 2

Results from Experiment #2

| Agents Administered | Survival | Comments |
| --- | --- | --- |
| none | 0% | Death in about a day |
| 10 ug scFv#2 | 0% | Death delayed about 2 days |
| 10 ug scFv#2 + 10 ug anti-E-tag mAb (mAb administered intraperitoneally) | 100% | Symptoms moderate |

TABLE 2-continued

Results from Experiment #2

| Agents Administered | Survival | Comments |
| --- | --- | --- |
| 10 ug scFv#2 + 10 ug anti-E-tag mAb | 100% | Symptoms mild |
| 10 ug scFv#2 + 2 ug anti-E-tag mAb | 100% | Symptoms mild |
| 2 ug scFv#2 + 10 ug anti-E-tag mAb | 100% | Symptoms moderate |
| 5 ug scFv#2 + 3 ug scFv#7 + 10 ug anti-E-tag mAb | 100% | No symptoms |
| 1 ug scFv#2 + 1 ug scFv#7 + 10 ug anti-E-tag mAb | 100% | No symptoms |
| 5 ug scFv#2 + 4 ug scFv#3 + 10 ug anti-E-tag mAb | 100% | No symptoms |
| 5 ug scFv#2 + 3 ug scFv#21 + 10 ug anti-E-tag mAb | 100% | No symptoms |

These results entirely confirm those from the first experiment and extend them as follows. The mAb against the epitopic tag does not have to be pre-mixed with the scFv containing the epitopic tag to be effective (it can be administered at a different site and time). Combinations of two scFvs (each with E-tags) and the single anti-E-tag mAb, provide greater protection than with one scFv alone. This synergistic protective effect occurs using different scFvs and at significantly lower doses of the scFvs or mAb than used previously.

In the third experiment, we tested combinations of three and four scFvs with anti-tag mAb to protect against 100, 1000 and 10,000 LD50 doses of BoNT/A.

TABLE 3

Results from Experiment #3

| BoNT/A | Agents Administered All received 10 μg of anti-E-tag mAb | Survival | Comments |
| --- | --- | --- | --- |
| 100 LD50 | None | 0% | Death in less than a day |
| 100 LD50 | 2 μg scFv#2 + scFv#3 + scFv#21 | 100% | No symptoms |
| 1000 LD50 | None | 0% | Death in less than a day |
| 1000 LD50 | 2 μg scFv#2 + scFv#3 + scFv#21 | 100% | No symptoms |
| 1000 LD50 | 2 μg scFv#2 + scFv#3 + scFv#7 + scFv#21 | 100% | No symptoms |
| 10,000 LD50 | None | 0% | Death in a few hours |
| 10,000 LD50 | 2 μg scFv#2 + scFv#3 + scFv#21 | 0% | Death delayed one day |
| 10,000 LD50 | 2 μg scFv#2 + scFv#3 + scFv#7 + scFv#21 | 100% | Moderate symptoms |

The results clearly demonstrate the excellent potency of the tagged binding agent approach as antitoxins. Specifically, we find that we can completely protect mice against even mild symptoms of intoxication by 1000 LD50s using combinations of three or four scFvs with anti-E-tag mAb. We can protect mice against lethality from a 10,000 LD50 dose with a combination of four scFvs, although the mice did develop moderate symptoms. The ability to protect mice receiving up to 10,000 LD50s of BoNT/A is equivalent to the highest level of protection reported with pools of different anti-BoNT/A mAbs (Nowakowski et al, Proc Natl Acad Sci USA, 99:11346-50).

The next experiment tested whether a binding agent containing two copies of the epitopic tag would improve efficacy. To perform this experiment, the anti-BoNT/A binding agent, scFv#7, was engineered to contain another copy of the E-tag peptide. In all previous studies, the E-tag peptide was present on the carboxyl terminus of each scFvs. A new version of scFv#7 (called scFv#7-2E) was engineered, identical to scFv#7 except for an additional copy of the E-tag peptide fused to the amino terminus.

TABLE 4

Results from Experiment #4

| BoNT/A LD50 | Agents Administered All received 10 μg of anti-E-tag mAb | Survival | Comments |
|---|---|---|---|
| 100 | None | 0% | Death in less than 6 hours |
| 100 | 1 μg scFv#2 + scFv#3 + scFv#7 | 100% | No symptoms |
| 100 | 1 μg scFv#2 + scFv#3 + scFv#7-2E | 100% | No symptoms |
| 1000 | None | 0% | Death in less than 2 hours |
| 1000 | 1 μg scFv#2 + scFv#3 + scFv#7 | 0% | Death delayed 2 days |
| 1000 | 1 μg scFv#2 + scFv#3 + scFv#7-2E | 100% | No symptoms |
| 10,000 | None | 0% | Death in less than 2 hours |
| 10,000 | 1 μg scFv#2 + scFv#3 + scFv#7 | 0% | Death delayed less than a day |
| 10,000 | 1 μg scFv#2 + scFv#3 + scFv#7-2E | 20% | Death delayed many days |
| 10,000 | 1 μg scFv#2 + scFv#3 + scFv #21 + scFv#7 | 0% | Death delayed 2 days |
| 10,000 | 1 μg scFv#2 + scFv#3 + scFv #21 + scFv#7-2E | 100% | Moderate symptoms |

The results demonstrate that the binding agent with two epitope tags dramatically improved the in vivo antitoxin efficacy of the tagged binding agent. With a combination of three scFvs, including scFvs#2, scFvs#3 and scFvs#7 or scFvs#7-2E, clearly the use of scFvs#7-2E was substantially superior in protection of mice to the use of scFvs#7 with only one E-tag. This was particularly evident in the groups of mice challenged with 1000 LD50. In these groups, the triple combination of scFv#2+scFv#3+scFv#7 was insufficient to allow survival of the mice. When scFv#7 was replaced with scFv#7-2E, all the mice survived without symptoms. Furthermore, use of a pool of scFv#2+scFv#3+scFv#7-2E permitted the survival of one of five mice challenged with 10,000 LD50 and delayed the death of the other mice by several days. The equivalent pool with scFv#7 having only one E-tag only delayed death for one day in mice challenged with 10,000 LD50. Finally, an identical combination of four scFvs (#2, #3, #21 and #7) in which the efficacy using scFv#7 was compared with scFv#7-2E. With only one μg of each scFv, the use of scFv#7 did not permit survival of mice challenged with 10,000 LD50 while the same combination using scFv#7-2E was protective. The implication of these results is that it is possible to protect mice against high doses of toxin simply by administering a smaller number high affinity binding agents, each containing two or more epitope tags together with an anti-tag mAb.

The new approach improves therapeutic agent flexibility, permits the use of highly stable binding agents with long shelf life, substantially reduces the cost of production, and permits therapeutic applications that involve multiple target agents to be more commercially feasible. Furthermore, the new strategy will permit much more rapid development of new antitoxins. The binding agents should be much quicker to develop to commercialization than mAbs. The single anti-tag mAb needed for co-administration is the same for therapies requiring different tagged binding agents and thus can be pre-selected for its commercial scale up properties and stockpiled in advance of the development of the binding agents.

An immediate application is in anti-toxin therapy, an area of high interest because of bioterrorist threats. For example, it is now thought that effective prevention of botulinum intoxication using toxin neutralizing mAbs will require administration of three different mAbs each targeting the same toxin. Since there are at least seven different botulinum toxins, this suggests that 21 different mAbs (or more) may need to be stockpiled for use in the event of a major botulism outbreak as might occur through bioterror. Monoclonal antibodies are very expensive to produce and have relatively short shelf lives. This concept would make it possible to produce 21 different recombinant binding agents, each having longer shelf-life and lower production costs, and then stockpile only a single mAb. It is possible that this approach could open up many other mAb therapeutic strategies that involve multiple binding targets, but which have not been pursued because of prohibitive development and production costs and poor product shelf life. It also permits the use of mAbs of different antibody isotypes to be used with the same binding agents to provide greater therapeutic flexibility.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for administering antibody therapeutic agents to treat an individual for exposure to a Botulinum neurotoxin, the method comprising:
   a. administering to the individual at least one binding agent, wherein the binding agent comprises a single-chain antibody (scFv) and has a binding region specific to the Botulinum neurotoxin and has one or more copies of a tag comprising an antibody epitope; and
   b. administering to the individual an anti-tag antibody, wherein the anti-tag antibody binds to the one or more copies of the tag of the binding agent and promotes clearance of the Botulinum neurotoxin, thereby treating the individual; and the binding agent binds to the portion of the Botulinum neurotoxin wherein the Botulinum neurotoxin is Botulinum neurotoxin serotype A, and wherein the scFv is encoded by a nucleic acid comprising a nucleotide sequence selected from the group of: SEQ ID NO: 1, SEQ ID NO: 3, SEQ ID NO: 5, SEQ NO: 7, SEQ ID NO: 9, SEQ ID NO: 11, and SEQ ID NO: 13.

2. The method according to claim 1, wherein the disease agent target is Botulinum neurotoxin a serotype A, and wherein the scFv comprises an amino acid sequence selected from the group of: SEQ ID NO: 2, SEQ ID NO: 4, SEQ ID NO: 6, SEQ ID NO: 8, SEQ ID NO: 10, SEQ ID NO: 12, and SEQ ID NO: 14.

* * * * *

SEQUENCE LISTING

```
<160> NUMBER OF SEQ ID NOS: 15

<210> SEQ ID NO 1
<211> LENGTH: 816
<212> TYPE: DNA
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (47)..(48)
```

<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 1

```
caggctgtgc tgactcagcc gtcctccgtg tccgggtccc cgggccnnan ggtctccatc    60
acctgctctg gaagcaggag taacgttggc acatatggtg taggttggtt ccaacagctc   120
ccaggatcgg gcctcagaac catcatctat tataatgaca aacgaccctc aggggtcccc   180
gaccgattct ctgcctccaa atcgggcaac acagccaccc tgatcatcag ctcgctccag   240
gctgaggatg aggccgatta tttctgtgga agtgccgacg gtagtagtta tggtattttc   300
ggcagtggga ccagactgac cgtcctgggt cagcccgcgg ccgctggtgg aggcggttca   360
ggcggaggtg gctctggcgg tggcggatcg gcgcgccagg tggggctgca ggagtcggga   420
cccagcctgg tgaagccctc acagaccctc tccctcacct gcacggtctc tggattctca   480
ttgtccaaca gtgttgtagg ctgggtccgc caggctccag aaaggtgcc ggagtggctt   540
ggtagtatag acagtggtgg ttacacagtc gctgacccgg ccctgaaatc ccgactcagc   600
atcacaaggg acacttccaa gagccaagtc tccctgtcac tgaacagcgt gacaactgag   660
gacacggccg tgtactactg tacaagggct tatagtatta cttattatgc gtatcccccc   720
tatatcgact actggggccc aggactcctg gtcaccgtct cctcaactag tggtgcgccg   780
gtgccgtatc cggatccgct ggaaccgcgt gccgca                             816
```

<210> SEQ ID NO 2
<211> LENGTH: 272
<212> TYPE: PRT
<213> ORGANISM: Artificial Sequence
<220> FEATURE:
<223> OTHER INFORMATION: scFv#2 single chain antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 2

```
Gln Ala Val Leu Thr Gln Pro Ser Ser Val Ser Gly Ser Pro Gly Xaa
1               5                   10                  15

Xaa Val Ser Ile Thr Cys Ser Gly Ser Arg Ser Asn Val Gly Thr Tyr
            20                  25                  30

Gly Val Gly Trp Phe Gln Gln Leu Pro Gly Ser Gly Leu Arg Thr Ile
        35                  40                  45

Ile Tyr Tyr Asn Asp Lys Arg Pro Ser Gly Val Pro Asp Arg Phe Ser
    50                  55                  60

Ala Ser Lys Ser Gly Asn Thr Ala Thr Leu Ile Ile Ser Ser Leu Gln
65                  70                  75                  80

Ala Glu Asp Glu Ala Asp Tyr Phe Cys Gly Ser Ala Asp Gly Ser Ser
                85                  90                  95

Tyr Gly Ile Phe Gly Ser Gly Thr Arg Leu Thr Val Leu Gly Gln Pro
            100                 105                 110

Ala Ala Ala Gly Gly Gly Ser Gly Gly Gly Ser Gly Gly
        115                 120                 125

Gly Ser Ala Arg Gln Val Gly Leu Gln Glu Ser Gly Pro Ser Leu Val
    130                 135                 140

Lys Pro Ser Gln Thr Leu Ser Leu Thr Cys Thr Val Ser Gly Phe Ser
145                 150                 155                 160
```

Leu Ser Asn Ser Val Val Gly Trp Val Arg Gln Ala Pro Gly Lys Val
          165                 170                 175

Pro Glu Trp Leu Gly Ser Ile Asp Ser Gly Gly Tyr Thr Val Ala Asp
          180                 185                 190

Pro Ala Leu Lys Ser Arg Leu Ser Ile Thr Arg Asp Thr Ser Lys Ser
          195                 200                 205

Gln Val Ser Leu Ser Leu Asn Ser Val Thr Thr Glu Asp Thr Ala Val
          210                 215                 220

Tyr Tyr Cys Thr Arg Ala Tyr Ser Ile Thr Tyr Ala Tyr Pro Pro
225                 230                 235                 240

Tyr Ile Asp Tyr Trp Gly Pro Gly Leu Leu Val Thr Val Ser Ser Thr
          245                 250                 255

Ser Gly Ala Pro Val Pro Tyr Pro Asp Pro Leu Glu Pro Arg Ala Ala
          260                 265                 270

<210> SEQ ID NO 3
<211> LENGTH: 826
<212> TYPE: DNA
<213> ORGANISM: Artificial Sequence
<220> FEATURE:
<223> OTHER INFORMATION: scFv#3 Single Chain Antibody

<400> SEQUENCE: 3

```
caggctgtgc tgactcagcc gtcctccgtg tccaggtccc tgggccagag tgtctccatc    60
acctgctctg gaagcagcag caacgttgga tatggtgatt atgtgggctg gttccaacgg   120
gtcccaggat cagcccccaa actcctcatc tatggtgcaa ccactcgagc ctcggggatc   180
cccgaccgat tctccggctc caggtctggc aacacagcga ctctgaccat cagctcgctc   240
caggctgagg acgaggccga ttattactgt tcatcttacg acagtagtca ctatagtatt   300
ttcggcagtg ggaccagcct gaccgtcctg ggtcagcccg cggccgctgg tggaggcggt   360
tcaggcggag gtggctctgg cggtggcgga tcggcgcgcc aggtggagct gcaggagtcg   420
ggacccagcc tggtgaagcc ctcacagacc ctctccctca cctgcacggt ctctggattc   480
tcattaagta gcaatgctgt aggctgggtc cgccaggctc aggaaaaggc gccggagtgg   540
gttggtggta tagatataga tggaaggccg gtctataaac caggccttaa gtcccggctc   600
agcatcacca gggacacctc caacgctcaa gtctccctgt cactgagcag cgtgacaact   660
gaggacacgg ccgtgtacta ctgtgcaagt tattatggtg ttatcttta taattatgcc   720
cctggggcat atatcgagca cttgagccca ggactcctga tcaccgtctc ctcaactagt   780
ggtgcgccgg tgccgtatcc ggatccgctg gaaaccgcgt gccgca             826
```

<210> SEQ ID NO 4
<211> LENGTH: 275
<212> TYPE: PRT
<213> ORGANISM: Artificial Sequence
<220> FEATURE:
<223> OTHER INFORMATION: scFv#3 single chain antibody

<400> SEQUENCE: 4

Gln Ala Val Leu Thr Gln Pro Ser Ser Val Ser Arg Ser Leu Gly Gln
1               5                   10                  15

Ser Val Ser Ile Thr Cys Ser Gly Ser Ser Asn Val Gly Tyr Gly
          20                  25                  30

Asp Tyr Val Gly Trp Phe Gln Arg Val Pro Gly Ser Ala Pro Lys Leu
          35                  40                  45

```
Leu Ile Tyr Gly Ala Thr Thr Arg Ala Ser Gly Val Pro Asp Arg Phe
        50                  55                  60

Ser Gly Ser Arg Ser Gly Asn Thr Ala Thr Leu Thr Ile Ser Ser Leu
 65                  70                  75                  80

Gln Ala Glu Asp Glu Ala Asp Tyr Tyr Cys Ser Ser Tyr Asp Ser Ser
                85                  90                  95

His Tyr Ser Ile Phe Gly Ser Gly Thr Ser Leu Thr Val Leu Gly Gln
               100                 105                 110

Pro Ala Ala Ala Gly Gly Gly Ser Gly Gly Gly Ser Gly Gly
           115                 120                 125

Gly Gly Ser Ala Arg Gln Val Glu Leu Gln Glu Ser Gly Pro Ser Leu
       130                 135                 140

Val Lys Pro Ser Gln Thr Leu Ser Leu Thr Cys Thr Val Ser Gly Phe
145                 150                 155                 160

Ser Leu Ser Ser Asn Ala Val Gly Trp Val Arg Gln Ala Pro Gly Lys
               165                 170                 175

Ala Pro Glu Trp Val Gly Gly Ile Asp Ile Asp Gly Arg Pro Val Tyr
           180                 185                 190

Lys Pro Gly Leu Lys Ser Arg Leu Ser Ile Thr Arg Asp Thr Ser Asn
           195                 200                 205

Ala Gln Val Ser Leu Ser Leu Ser Ser Val Thr Thr Glu Asp Thr Ala
       210                 215                 220

Val Tyr Phe Cys Ala Ser Tyr Tyr Gly Gly Tyr Leu Tyr Asn Tyr Ala
225                 230                 235                 240

Pro Gly Ala Tyr Ile Glu His Leu Ser Pro Gly Leu Leu Ile Thr Val
               245                 250                 255

Ser Ser Thr Ser Gly Ala Pro Val Pro Tyr Pro Asp Pro Leu Glu Pro
           260                 265                 270

Arg Ala Ala
        275

<210> SEQ ID NO 5
<211> LENGTH: 816
<212> TYPE: DNA
<213> ORGANISM: Artificial Sequence
<220> FEATURE:
<223> OTHER INFORMATION: scFv#7 Single Chain Antibody

<400> SEQUENCE: 5
tcctatgaac tgacccagcc gccttcaatg tcggtggcct tgggacagac ggccaaggtc    60
acctgccagg gagacaactt agaaaacttt tatgttcagt ggcaccagca gaagccgggc   120 caggccctg tgacggtcat ttttcaggat aataagaggc cctcgggat ccctgaccgg    180 ttctctggct ccaactcggg aacacggcc accctgacca tcagcgggc ccggaccgag    240 gacgaggccg actattactg tcagtcaggc cacagcagta tcggtggtgt tttcggcagc   300
gggaccagcc tgaccgtcct gggtcagccc gcggccgctg gtggaggcgg ttcaggcgga    360
ggtggctctg gcggtggcgg atcggcgcgc caggtgcagc tgcaggagtc gggacccagc    420
ctggtgaagc cctcacagac cctctcccct acctgcacgg tctctggctt ctcattaacg    480
ggaaattctg taacctgggt ccgccaggct ccaggaaacg tgccgagtg gcttggtggt    540 ataagccgcg gtggacgcac atactatgat acggccctga gtccggct cagcatcacc    600 agggacacct ccaagaggca agtctcccta tcactgagca gcgtgacgac tgaggacacg    660
gccatgtact tctgtgcaag atcggcatat agtactcttt atgattatga gtatgccgct    720
```

```
gatatctacg actgggggccc aggactcctg gtcaccgtct cctcaactag tggtgcgccg      780
gtgccgtatc cggatccgct ggaaccgcgt gccgca                                  816
```

<210> SEQ ID NO 6
<211> LENGTH: 272
<212> TYPE: PRT
<213> ORGANISM: Artificial Sequence
<220> FEATURE:
<223> OTHER INFORMATION: scFv#7 Single Chain Antibody

<400> SEQUENCE: 6

Ser Tyr Glu Leu Thr Gln Pro Pro Ser Met Ser Val Ala Leu Gly Gln
1               5                   10                  15

Thr Ala Lys Val Thr Cys Gln Gly Asp Asn Leu Glu Asn Phe Tyr Val
            20                  25                  30

Gln Trp His Gln Gln Lys Pro Gly Gln Ala Pro Val Thr Val Ile Phe
        35                  40                  45

Gln Asp Asn Lys Arg Pro Ser Gly Ile Pro Asp Arg Phe Ser Gly Ser
    50                  55                  60

Asn Ser Gly Asn Thr Ala Thr Leu Thr Ile Ser Gly Ala Arg Thr Glu
65                  70                  75                  80

Asp Glu Ala Asp Tyr Tyr Cys Gln Ser Gly His Ser Ser Ile Gly Gly
                85                  90                  95

Val Phe Gly Ser Gly Thr Ser Leu Thr Val Leu Gly Gln Pro Ala Ala
            100                 105                 110

Ala Gly Gly Gly Gly Ser Gly Gly Gly Ser Gly Gly Gly Gly Ser
        115                 120                 125

Ala Arg Gln Val Gln Leu Gln Glu Ser Gly Pro Ser Leu Val Lys Pro
    130                 135                 140

Ser Gln Thr Leu Ser Leu Thr Cys Thr Val Ser Gly Phe Ser Leu Thr
145                 150                 155                 160

Gly Asn Ser Val Thr Trp Val Arg Gln Ala Pro Gly Asn Val Pro Glu
                165                 170                 175

Trp Leu Gly Gly Ile Ser Arg Gly Gly Arg Thr Tyr Tyr Asp Thr Ala
            180                 185                 190

Leu Lys Ser Arg Leu Ser Ile Thr Arg Asp Thr Ser Lys Arg Gln Val
        195                 200                 205

Ser Leu Ser Leu Ser Ser Val Thr Thr Glu Asp Thr Ala Met Tyr Phe
    210                 215                 220

Cys Ala Arg Ser Ala Tyr Ser Thr Leu Tyr Asp Tyr Glu Tyr Ala Ala
225                 230                 235                 240

Asp Ile Tyr Asp Trp Gly Pro Gly Leu Leu Val Thr Val Ser Ser Thr
                245                 250                 255

Ser Gly Ala Pro Val Pro Tyr Pro Asp Pro Leu Glu Pro Arg Ala Ala
            260                 265                 270

<210> SEQ ID NO 7
<211> LENGTH: 795
<212> TYPE: DNA
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)

<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 7

```
tcctatgaac tgacccagcc gccttcagtg tcggtggttt ggggncngan ggccgagatc    60
acctgccagg gagacctact ggataaaaaa tatacagctt ggtaccagca gaagccgggc   120
caggctccta tgaaaatcat taataaagac agtgagcggc cttcagggat ccggaccgg    180
ttctcgggct ccagctcagg caaaacagcc accctaacca tcaacggggc ccggcctgag   240
gacgaggccg actattactg tttatcaggt gacagcaata ataatggtgt cttcggcagc   300
gggaccagcc tgaccgtcct gggtcagccc gcggccgctg gtggaggcgg ttcaggcgga   360
ggtggctctg gcggtggcgg atcggcgcgc caggtggagc tgcaggggtc gggacccagc   420
ctggtgaagc cctcgcagac cctctccctc acctgcacgg tctctggatt ctcatggccc   480
aacaatgctg tggattgggt ccgccaggct ccaggaaagg cgccggagtg gcttggtggt   540
attgccgata atggaagaac aaactacaac acgccctaa aagcccggct cagcatcact    600
agggacaccc caagagcca tgtctcccta tcgctgagca gcgtgacagc tgaggatacg   660
gccgtttact attgtacagc gggggttatg gtcatgcacg ccactgacta ctggggcccg   720
ggactcctgg tcaccgtctc ctcaactagt ggtgcgccgg tgccgtatcc ggatccgctg   780
gaaccgcgtg ccgca                                                    795
```

<210> SEQ ID NO 8
<211> LENGTH: 265
<212> TYPE: PRT
<213> ORGANISM: Artificial Sequence
<220> FEATURE:
<223> OTHER INFORMATION: scFv#8 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 8

```
Ser Tyr Glu Leu Thr Gln Pro Pro Ser Val Ser Val Trp Gly Xaa
1               5                   10                  15
Xaa Ala Glu Ile Thr Cys Gln Gly Asp Leu Leu Asp Lys Lys Tyr Thr
            20                  25                  30
Ala Trp Tyr Gln Gln Lys Pro Gly Gln Ala Pro Met Lys Ile Ile Asn
        35                  40                  45
Lys Asp Ser Glu Arg Pro Ser Gly Ile Arg Asp Arg Phe Ser Gly Ser
    50                  55                  60
Ser Ser Gly Lys Thr Ala Thr Leu Thr Ile Asn Gly Ala Arg Pro Glu
65                  70                  75                  80
Asp Glu Ala Asp Tyr Tyr Cys Leu Ser Gly Asp Ser Asn Asn Asn Gly
                85                  90                  95
Val Phe Gly Ser Gly Thr Ser Leu Thr Val Leu Gly Gln Pro Ala Ala
            100                 105                 110
Ala Gly Gly Gly Gly Ser Gly Gly Gly Ser Gly Gly Gly Gly Ser
        115                 120                 125
Ala Arg Gln Val Glu Leu Gln Gly Ser Gly Pro Ser Leu Val Lys Pro
    130                 135                 140
Ser Gln Thr Leu Ser Leu Thr Cys Thr Val Ser Gly Phe Ser Trp Pro
145                 150                 155                 160
```

Asn Asn Ala Val Asp Trp Val Arg Gln Ala Pro Gly Lys Ala Pro Glu
            165                 170                 175

Trp Leu Gly Gly Ile Ala Asp Asn Gly Arg Thr Asn Tyr Asn Thr Ala
            180                 185                 190

Leu Lys Ala Arg Leu Ser Ile Thr Arg Asp Thr Ala Lys Ser His Val
            195                 200                 205

Ser Leu Ser Leu Ser Ser Val Thr Ala Glu Asp Thr Ala Val Tyr Tyr
            210                 215                 220

Cys Thr Ala Gly Val Met Val Met His Ala Thr Asp Tyr Trp Gly Pro
225                 230                 235                 240

Gly Leu Leu Val Thr Val Ser Ser Thr Ser Gly Ala Pro Val Pro Tyr
            245                 250                 255

Pro Asp Pro Leu Glu Pro Arg Ala Ala
            260                 265

<210> SEQ ID NO 9
<211> LENGTH: 810
<212> TYPE: DNA
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 9
caggctgtgg tgactcagcc gtcctccgtg tccgggtccc cgggccnnan agtctccatc      60
acctgctctg gaagcagcag caacgttggt agatatgctg taggctggtt ccaacagctc     120
ccaggatcgg gcctcagaac cgtcatctat tataatagca atcgaccctc aggggtcccc     180
gaccgattct ctggctccaa atcgggcaac acagccaccc tgaccatcag ctcgctccag     240
gctgaggatg aggccgatta tttctgtgga agttatgaca gtagtatcta tggtgttttc     300
ggcagcggga ccaggctgac cgtcctgggt cagcccgcgg ccgctggtgg aggcggttca     360
ggcggaggtg gctctggcgg tggcggatcg gcgcgccagg tgcagctgca ggagtcggga     420
cccagcctgg tgaggccctc acagaccctc tccctcacct gcacgatctc tggattctct     480
ttaagagagt atggtgtagg ttgggtccgc caggctccag gaaaggcgtt ggagtggctt     540
gggcgaatag atgattctgg atacacatta cataatcctg cccttaagtc ccggctcacc     600
ataactaggg acatctccaa gagccaagtc tccctgtcac tgagcagcgt gacacttgag     660
gacacggccg aatattactg cgtatatgct agtcgtggta ctgcttggtt gggagacatc     720
gatgtctggg gcccaggact cctgctcact gtctcctcaa ctagtggtgc gccggtgccg     780
tatccggatc cgctggaacc gcgtgccgca                                      810

<210> SEQ ID NO 10
<211> LENGTH: 270
<212> TYPE: PRT
<213> ORGANISM: Artificial Sequence
<220> FEATURE:
<223> OTHER INFORMATION: scFv#21 Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 10

```
Gln Ala Val Val Thr Gln Pro Ser Ser Val Ser Gly Ser Pro Gly Xaa
1               5                   10                  15
Xaa Val Ser Ile Thr Cys Ser Gly Ser Ser Asn Val Gly Arg Tyr
                20                  25                  30
Ala Val Gly Trp Phe Gln Gln Leu Pro Gly Ser Gly Leu Arg Thr Val
            35                  40                  45
Ile Tyr Tyr Asn Ser Asn Arg Pro Ser Gly Val Pro Asp Arg Phe Ser
        50                  55                  60
Gly Ser Lys Ser Gly Asn Thr Ala Thr Leu Thr Ile Ser Ser Leu Gln
65                  70                  75                  80
Ala Glu Asp Glu Ala Asp Tyr Phe Cys Gly Ser Tyr Asp Ser Ser Ile
                85                  90                  95
Tyr Gly Val Phe Gly Ser Gly Thr Arg Leu Thr Val Leu Gly Gln Pro
            100                 105                 110
Ala Ala Ala Gly Gly Gly Ser Gly Gly Gly Ser Gly Gly Gly
        115                 120                 125
Gly Ser Ala Arg Gln Val Gln Leu Gln Glu Ser Gly Pro Ser Leu Val
130                 135                 140
Arg Pro Ser Gln Thr Leu Ser Leu Thr Cys Thr Ile Ser Gly Phe Ser
145                 150                 155                 160
Leu Arg Glu Tyr Gly Val Gly Trp Val Arg Gln Ala Pro Gly Lys Ala
                165                 170                 175
Leu Glu Trp Leu Gly Arg Ile Asp Asp Ser Gly Tyr Thr Leu His Asn
            180                 185                 190
Pro Ala Leu Lys Ser Arg Leu Thr Ile Thr Arg Asp Ile Ser Lys Ser
        195                 200                 205
Gln Val Ser Leu Ser Leu Ser Ser Val Thr Leu Glu Asp Thr Ala Glu
    210                 215                 220
Tyr Tyr Cys Val Tyr Ala Ser Arg Gly Thr Ala Trp Leu Gly Asp Ile
225                 230                 235                 240
Asp Val Trp Gly Pro Gly Leu Leu Leu Thr Val Ser Ser Thr Ser Gly
                245                 250                 255
Ala Pro Val Pro Tyr Pro Asp Pro Leu Glu Pro Arg Ala Ala
            260                 265                 270
```

<210> SEQ ID NO 11
<211> LENGTH: 816
<212> TYPE: DNA
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 11

```
caggctgtgc tgactcagcc gtcctccgtg tccaggtccc tgggccnnan tgtctcgatc    60
acctgctctg gaggcagcag caacgttgga caaggtgatt atgtggcctg gttccaacag   120
gtcccaggat cagcccccaa actcctcatc tatgatgcga cgaatcgagc ctcgggggtc   180
cccgaccgat tcgtcggctc cagatatggc aactcagcga ctctgatcat cacctcggtc   240
```

```
caggctgagg acgaggccga ttattattgt gcatcttatg acagtagtat gtatacgatt    300
ttcggcagcg ggaccagcct gaccgtcctg ggtcagcccg cggccgctgg tggaggcggt    360
tcaggcggag gtggctctgg cggtggcgga tcggcgcgcc aggtggagct gcaggggtcg    420
ggacccagcc aggtgaagcc ctcacagacc ctctccctca tctgcacgat ctctggattc    480
tcattaacca gcaataatgt agcctgggtc cgccaggctc aggaaaggg actggagtgg    540 gttggtgtca taagtgatgg tggaactcca tactataact cggccctgaa atcccggctc    600
agcatcacca gggacacctc caagagccag gtctccctgt cactgagcag cgtgacaact    660
gaggacacgg ccgtgtacta ctgtgcacgg acgttggatt atagtcatat ttggttgtac    720
tccgccgacc aatggggccc aggactcctg gtcaccgtct cctcaactag tggtgcgccg    780
gtgccgtatc cggatccgct ggaaccgcgt gccgca                              816
```

<210> SEQ ID NO 12
<211> LENGTH: 272
<212> TYPE: PRT
<213> ORGANISM: Artificial Sequence
<220> FEATURE:
<223> OTHER INFORMATION: scFv#E Single Chain Antibody
<220> FEATURE:
<221> NAME/KEY: misc_feature
<222> LOCATION: (16)..(17)
<223> OTHER INFORMATION: Xaa can be any naturally occurring amino acid

<400> SEQUENCE: 12

```
Gln Ala Val Leu Thr Gln Pro Ser Ser Val Ser Arg Ser Leu Gly Xaa
1               5                   10                  15

Xaa Val Ser Ile Thr Cys Ser Gly Gly Ser Ser Asn Val Gly Gln Gly
            20                  25                  30

Asp Tyr Val Ala Trp Phe Gln Gln Val Pro Gly Ser Ala Pro Lys Leu
        35                  40                  45

Leu Ile Tyr Asp Ala Thr Asn Arg Ala Ser Gly Val Pro Asp Arg Phe
    50                  55                  60

Val Gly Ser Arg Tyr Gly Asn Ser Ala Thr Leu Ile Ile Thr Ser Val
65                  70                  75                  80

Gln Ala Glu Asp Glu Ala Asp Tyr Tyr Cys Ala Ser Tyr Asp Ser Ser
                85                  90                  95

Met Tyr Thr Ile Phe Gly Ser Gly Thr Ser Leu Thr Val Leu Gly Gln
            100                 105                 110

Pro Ala Ala Ala Gly Gly Gly Gly Ser Gly Gly Gly Ser Gly Gly
        115                 120                 125

Gly Gly Ser Ala Arg Gln Val Glu Leu Gln Gly Ser Gly Pro Ser Gln
    130                 135                 140

Val Lys Pro Ser Gln Thr Leu Ser Leu Ile Cys Thr Ile Ser Gly Phe
145                 150                 155                 160

Ser Leu Thr Ser Asn Asn Val Ala Trp Val Arg Gln Ala Pro Gly Lys
                165                 170                 175

Gly Leu Glu Trp Val Gly Val Ile Ser Asp Gly Gly Thr Pro Tyr Tyr
            180                 185                 190

Asn Ser Ala Leu Lys Ser Arg Leu Ser Ile Thr Arg Asp Thr Ser Lys
        195                 200                 205

Ser Gln Val Ser Leu Ser Leu Ser Ser Val Thr Thr Glu Asp Thr Ala
    210                 215                 220

Val Tyr Tyr Cys Ala Arg Thr Leu Asp Tyr Ser His Ile Trp Leu Tyr
225                 230                 235                 240
```

Ser Ala Asp Gln Trp Gly Pro Gly Leu Leu Val Thr Val Ser Ser Thr
              245                 250                 255

Ser Gly Ala Pro Val Pro Tyr Pro Asp Pro Leu Glu Pro Arg Ala Ala
            260                 265                 270

<210> SEQ ID NO 13
<211> LENGTH: 861
<212> TYPE: DNA
<213> ORGANISM: Artificial Sequence
<220> FEATURE:
<223> OTHER INFORMATION: scFv#7-2E Single Chain Antibody

<400> SEQUENCE: 13

```
ggtgcgccgg tgccgtatcc ggatccgctc gagccgcgtg ccggctccta tgaactgacc      60
cagccgcctt caatgtcggt ggccttggga cagacggcca aggtcacctg ccagggagac     120
aacttagaaa acttttatgt tcagtggcac agcagaagc cgggccaggc ccctgtgacg      180
gtcattttc aggataataa gaggccctcg gggatccctg accggttctc tggctccaac      240
tcggggaaca cggccaccct gaccatcagc ggggcccgga ccgaggacga ggccgactat     300
tactgtcagt caggccacag cagtatcggt ggtgttttcg gcagcgggac cagcctgacc     360
gtcctgggtc agcccgcggc cgctggtgga ggcggttcag gcggaggtgg ctctggcggt    420
ggcggatcgg cgcgccaggt gcagctgcag gagtcgggac ccagcctggt gaagccctca    480
cagaccctct ccctcacctg cacggtctct ggcttctcat aacgggaaa ttctgtaacc     540
tgggtccgcc aggctccagg aaacgtgccg gagtggcttg gtggtataag ccgcggtgga   600
cgcacatact atgatacggc cctgaagtcc cggctcagca tcaccaggga cacctccaag   660
aggcaagtct ccctatcact gagcagcgtg acgactgagg acacggccat gtacttctgt   720
gcaagatcgg catatagtac tctttatgat tatgagtatg ccgctgatat ctacgactgg   780
ggcccaggac tcctggtcac cgtctcctca actagtggtg cgccggtgcc gtatccggat   840
ccgctggaac cgcgtgccgc a                                              861
```

<210> SEQ ID NO 14
<211> LENGTH: 287
<212> TYPE: PRT
<213> ORGANISM: Artificial Sequence
<220> FEATURE:
<223> OTHER INFORMATION: scFv#7-2E Single Chain Antibody

<400> SEQUENCE: 14

Gly Ala Pro Val Pro Tyr Pro Asp Pro Leu Glu Pro Arg Ala Gly Ser
1               5                  10                  15

Tyr Glu Leu Thr Gln Pro Pro Ser Met Ser Val Ala Leu Gly Gln Thr
            20                  25                  30

Ala Lys Val Thr Cys Gln Gly Asp Asn Leu Glu Asn Phe Tyr Val Gln
        35                  40                  45

Trp His Gln Gln Lys Pro Gly Gln Ala Pro Val Thr Val Ile Phe Gln
    50                  55                  60

Asp Asn Lys Arg Pro Ser Gly Ile Pro Asp Arg Phe Ser Gly Ser Asn
65                  70                  75                  80

Ser Gly Asn Thr Ala Thr Leu Thr Ile Ser Gly Ala Arg Thr Glu Asp
                85                  90                  95

Glu Ala Asp Tyr Tyr Cys Gln Ser Gly His Ser Ser Ile Gly Gly Val
            100                 105                 110

Phe Gly Ser Gly Thr Ser Leu Thr Val Leu Gly Gln Pro Ala Ala Ala

```
                    115                 120                 125
Gly Gly Gly Gly Ser Gly Gly Gly Ser Gly Gly Gly Ser Ala
            130                 135                 140

Arg Gln Val Gln Leu Gln Glu Ser Gly Pro Ser Leu Val Lys Pro Ser
145                 150                 155                 160

Gln Thr Leu Ser Leu Thr Cys Thr Val Ser Gly Phe Ser Leu Thr Gly
                165                 170                 175

Asn Ser Val Thr Trp Val Arg Gln Ala Pro Gly Asn Val Pro Glu Trp
                180                 185                 190

Leu Gly Gly Ile Ser Arg Gly Gly Arg Thr Tyr Tyr Asp Thr Ala Leu
                195                 200                 205

Lys Ser Arg Leu Ser Ile Thr Arg Asp Thr Ser Lys Arg Gln Val Ser
            210                 215                 220

Leu Ser Leu Ser Ser Val Thr Thr Glu Asp Thr Ala Met Tyr Phe Cys
225                 230                 235                 240

Ala Arg Ser Ala Tyr Ser Thr Leu Tyr Asp Tyr Glu Tyr Ala Ala Asp
                245                 250                 255

Ile Tyr Asp Trp Gly Pro Gly Leu Leu Val Thr Val Ser Ser Thr Ser
                260                 265                 270

Gly Ala Pro Val Pro Tyr Pro Asp Pro Leu Glu Pro Arg Ala Ala
                275                 280                 285

<210> SEQ ID NO 15
<211> LENGTH: 13
<212> TYPE: PRT
<213> ORGANISM: Artificial Sequence
<220> FEATURE:
<223> OTHER INFORMATION: Epitope Tag

<400> SEQUENCE: 15

Gly Ala Pro Val Pro Tyr Pro Asp Pro Leu Glu Pro Arg
1               5                   10
```